US012674773B2

(12) United States Patent
Hayashi

(10) Patent No.: US 12,674,773 B2
(45) Date of Patent: Jul. 7, 2026

(54) SENSOR

(71) Applicant: KABUSHIKI KAISHA TOSHIBA,
Tokyo (JP)

(72) Inventor: Yumi Hayashi, Ayase Kanagawa (JP)

(73) Assignee: KABUSHIKI KAISHA TOSHIBA,
Kawasaki (JP)

( * ) Notice: Subject to any disclaimer, the term of this
patent is extended or adjusted under 35
U.S.C. 154(b) by 373 days.

(21) Appl. No.: 18/423,924

(22) Filed: Jan. 26, 2024

(65) Prior Publication Data

US 2025/0052710 A1 Feb. 13, 2025

(30) Foreign Application Priority Data

Aug. 10, 2023 (JP) ................................. 2023-131132

(51) Int. Cl.
*G01N 27/22* (2006.01)
*G01N 33/00* (2006.01)

(52) U.S. Cl.
CPC ....... *G01N 27/226* (2013.01); *G01N 33/0027*
(2013.01)

(58) Field of Classification Search
CPC ......................... G01N 27/226; G01N 33/0027
See application file for complete search history.

(56) References Cited

U.S. PATENT DOCUMENTS

| | | | |
|---|---|---|---|
| 11,448,628 B2 * | 9/2022 | Hiramatsu | G01N 27/18 |
| 11,906,495 B2 * | 2/2024 | Hayashi | G01N 33/0073 |
| 12,461,052 B2 * | 11/2025 | Hayashi | G01N 33/005 |
| 2019/0086377 A1 | 3/2019 | Ikehashi et al. | |
| 2022/0018820 A1 * | 1/2022 | Hiramatsu | G01N 27/228 |
| 2024/0068973 A1 * | 2/2024 | Hayashi | G01N 27/227 |
| 2024/0201119 A1 * | 6/2024 | Hayashi | G01N 27/226 |

FOREIGN PATENT DOCUMENTS

| | | |
|---|---|---|
| JP | 2019-56607 A | 4/2019 |
| WO | WO 2009/126568 A1 | 10/2009 |

* cited by examiner

*Primary Examiner* — Stephanie E Bloss
*Assistant Examiner* — Diana Hancock
(74) *Attorney, Agent, or Firm* — Finnegan, Henderson,
Farabow, Garrett & Dunner, LLP

(57) ABSTRACT

According to one embodiment, a sensor includes a base, a
fixed electrode, a first fixed portion, a first support portion,
and a movable portion supported by the first support portion.
The base includes first and second regions. The fixed elec-
trode and the first fixed portion are fixed to the first region
and the second region, respectively. The first support portion
is connected to the first fixed portion, and includes a first
support layer, a first layer, and a second layer. The first layer
is provided between the first support layer and at least a part
of the second layer in a first direction from the first support
layer to the second layer. The first layer includes oxygen and
a first element including at least one selected from the group
consisting of Pt, Pd and Ti. The second layer includes
oxygen and a second element different from the first ele-
ment.

20 Claims, 3 Drawing Sheets

SENSOR

CROSS-REFERENCE TO RELATED APPLICATIONS

This application is based upon and claims the benefit of priority from Japanese Patent Application No. 2023-131132, filed on Aug. 10, 2023; the entire contents of which are incorporated herein by reference.

FIELD

Embodiments described herein generally relate to a sensor.

BACKGROUND

For example, there are sensors that apply a MEMS structure. High detection sensitivity is desired in sensors.

DETAILED DESCRIPTION

Figure 1:
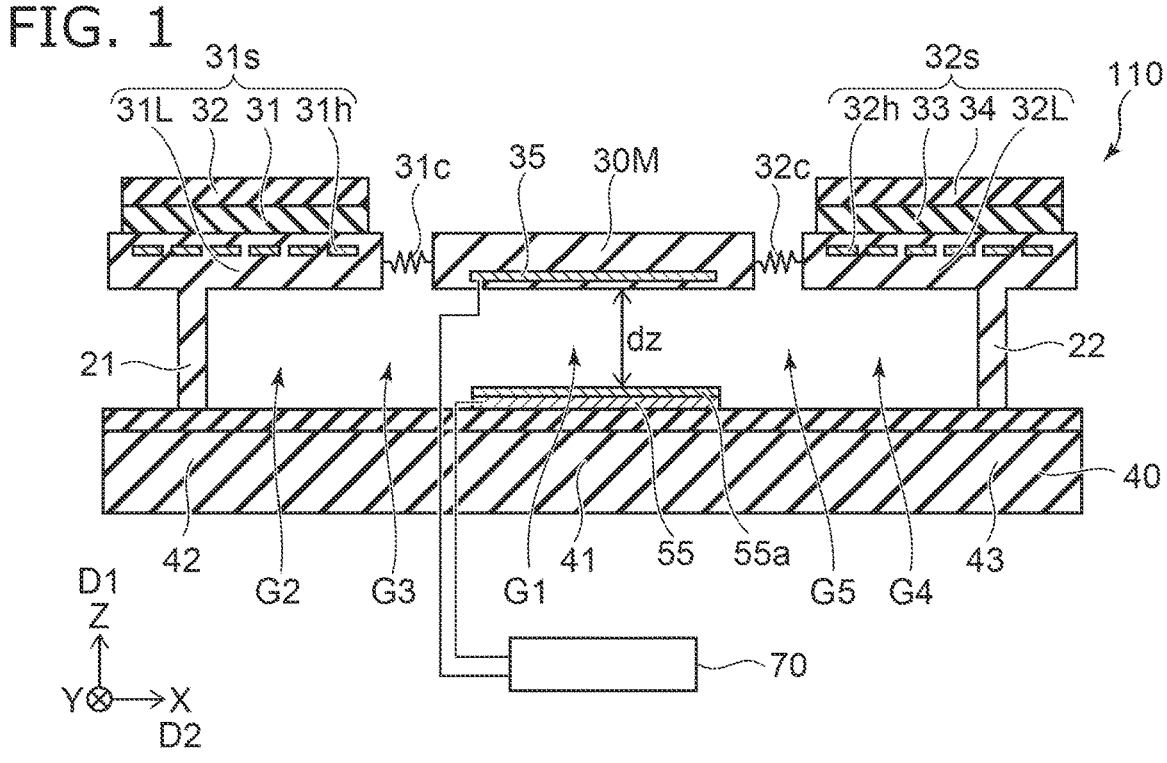
FIG. 1 is a schematic cross-sectional view illustrating a sensor according to a first embodiment.

According to one embodiment, a sensor includes a base, a fixed electrode, a first fixed portion, a first support portion, and a movable portion. The base includes a first region and a second region. The fixed electrode is fixed to the first region. The first fixed portion is fixed to the second region. The first support portion is connected to the first fixed portion. The first support portion includes a first support layer, a first layer, and a second layer. The first layer is provided between the first support layer and at least a part of the second layer in a first direction from the first support layer to the second layer. The first layer includes oxygen and a first element including at least one selected from the group consisting of Pt, Pd and Ti. The second layer includes oxygen and a second element different from the first element. The movable portion is supported by the first support portion. A first gap is provided between the fixed electrode and the movable portion.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously in an antecedent drawing are marked with like reference numerals, and a detailed description is omitted as appropriate.

First Embodiment

FIG. 1 is a schematic cross-sectional view illustrating a sensor according to a first embodiment.

As shown in FIG. 1, a sensor 110 according to the embodiment includes a base 40, a fixed electrode 55, a first fixed portion 21, a first support portion 31s, and a movable portion 30M.

The base 40 includes a first region 41 and a second region 42. The base 40 may be, for example, a silicon substrate.

The fixed electrode 55 is fixed to first region 41. An insulating film 55a may be provided on the fixed electrode 55.

The first fixed portion 21 is fixed to the second region 42. The first support portion 31s is connected to the first fixed portion 21. The first support portion 31s includes a first support layer 31L, a first layer 31, and a second layer 32. The first layer 31 is fixed to the first support layer 31L. In a first direction D1 from the first support layer 31L to the second layer 32, the first layer 31 is provided between the first support layer 31L and at least a part of the second layer 32.

The first layer 31 includes oxygen and a first element including at least one selected from the group consisting of Pt, Pd, and Ti. For example, the first layer 31 includes an oxide of the first element. For example, the first layer 31 includes a bond of the first element and oxygen.

The second layer 32 includes oxygen and a second element different from the first element. In one example, the second element includes at least one selected from the group consisting of Si and Al. For example, the second layer 32 includes an oxide of the second element. For example, the second layer 32 includes a bond of the second element and oxygen.

The movable portion 30M is supported by the first support portion 31s. A first gap G1 is provided between the fixed electrode 55 and the movable portion 30M.

For example, the first layer 31 is reduced by the detection target gas around the first support portion 31s. At least a part of the oxide of the first element included in the first layer 31 is reduced. The detection target gas includes, for example, hydrogen. When the first layer 31 is reduced, for example, oxygen included in the first layer 31 is released from the first layer 31. The structure of the first layer 31 changes. For example, the volume of the first layer 31 changes.

Due to the change in the structure of the first layer 31, stress is generated between the first layer 31 and the first support layer 31L. The stress is, for example, tensile stress. For example, the first layer 31 tries to shrink with respect to the first support layer 31L. Thereby, the shape of the first support portion 31s changes. Due to the change in shape, the distance between the movable portion 30M and the fixed electrode 55 changes. The capacitance changes as the distance changes. The detection target gas can be detected by detecting the change in capacitance.

In the embodiment, the second layer 32 described above is provided. It has been found that this results in higher detection sensitivity.

Figure 2:
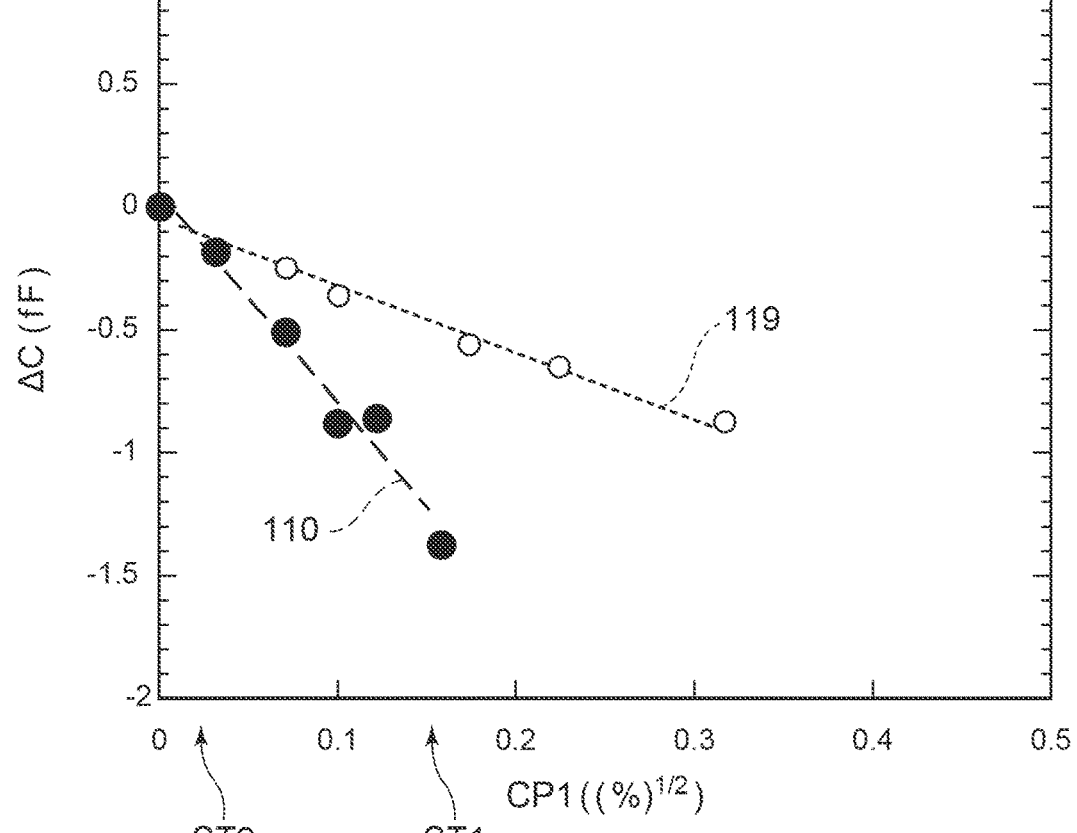
FIG. 2 is a graph illustrating the characteristics of the sensor.

FIG. 2 is a graph illustrating the characteristics of the sensor.

The horizontal axis in FIG. 2 is a concentration parameter CP1. The concentration parameter CP1 is the ½ power of the concentration of the detection target gas. An increase in concentration parameter CP1 corresponds to an increase in the concentration of the detection target gas. The vertical axis is the change in capacitance ΔC. The change ΔC is based on the capacitance when the concentration of the detection target gas is 0. A negative change ΔC corresponds to a decrease in capacitance.

FIG. 2 shows the characteristics of the sensor 110 according to the embodiment and the characteristics of a sensor 119 of a first reference example.

As shown in FIG. 2, when the concentration parameter CP1 increases, the change in capacitance ΔC is negative and the absolute value of the change ΔC increases. That is, when the concentration of the detection target gas increases, the capacitance decreases.

As shown in FIG. 2, in the sensor 110, the ratio (slope) of the change in the change ΔC to the change in the concentration parameter CP1 is higher than the ratio (slope) in the sensor 119. The sensor 110 can detect the detection target with high sensitivity.

Oxygen present in the air is present around the first support portion 31s in addition to the detection target gas (for example, reducing gas). In the first reference example in which the second layer 32 is not provided, it is thought that oxygen is adsorbed to the first layer 31. In the first reference example, it is thought that reduction of the first layer 31 (first element) and desorption of oxygen adsorbed on the first layer 31 occur simultaneously. The stress changes in the first support portion 31s due to these phenomena are in the opposite direction. Therefore, in the first reference example, it is difficult to make the sensitivity sufficiently high.

On the other hand, by providing the second layer 32, the influence of oxygen on the first layer 31 is suppressed. It is considered that this allows high detection sensitivity to be obtained in the embodiment.

Figure 3A:
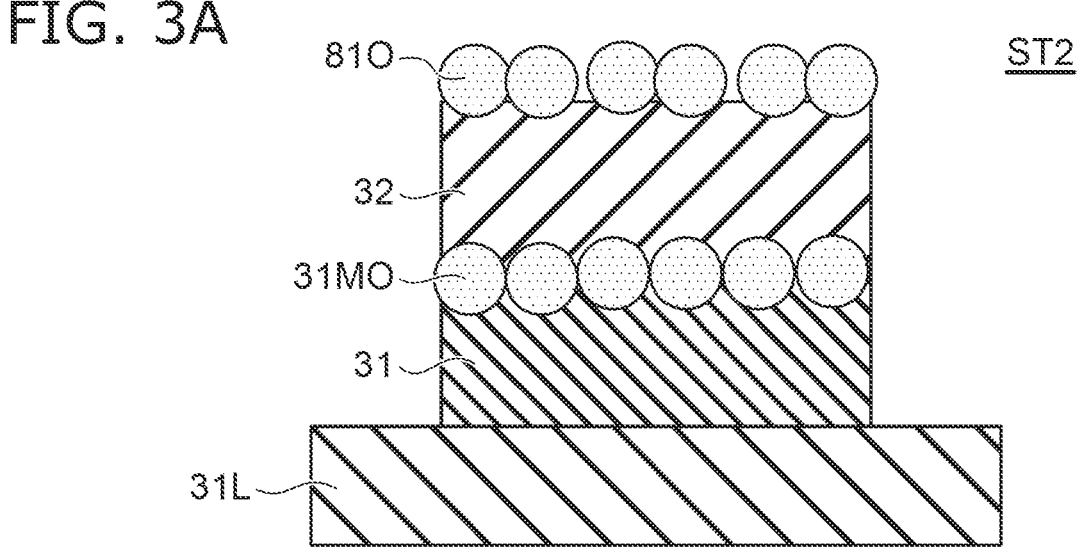
FIGS. 3A and 3B are schematic cross-sectional views illustrating the operation of the sensor according to the first embodiment.
Figure 3B:
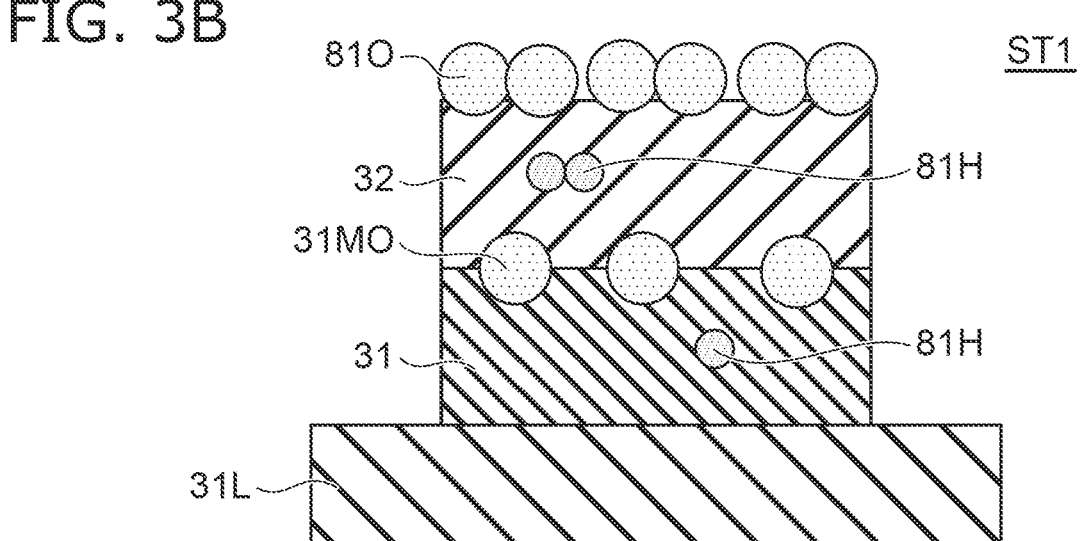

FIGS. 3A and 3B are schematic cross-sectional views illustrating the operation of the sensor according to the first embodiment.

In the second state ST2 shown in FIG. 3A, the concentration of the detection target gas (for example, hydrogen) is low. In the second state ST2, there is substantially no detection target gas (for example, hydrogen). In the first state ST1 shown in FIG. 3B, the detection target gas (for example, hydrogen) exists. In the first state ST1, the concentration of the detection target gas (for example, hydrogen) is higher than the concentration in the second state ST2.

As shown in FIG. 3A, in the second state ST2, an oxide 31MO of the first element (for example, Pt oxide) is present in the first layer 31. Oxygen 810 in the air is adsorbed on the surface of the second layer 32.

As shown in FIG. 3B, in the first state ST1, the detection target gas 81H (for example, hydrogen) passes through the second layer 32 and reaches the first layer 31. Reduction of the first element occurs in the first layer 31. The detection target gas 81H is in a molecular state (hydrogen molecules) on the surface of the second layer 32. Therefore, there is substantially no effect on the oxygen adsorbed on the surface of the second layer 32. Therefore, oxygen desorption is suppressed. In the embodiment, the reduction change is efficiently utilized by suppressing the release of oxygen. According to the embodiment, a sensor having high detection sensitivity can be provided.

In the embodiment, the reduction of the first element oxide occurs while desorption of adsorbed oxygen is suppressed. Thereby, a highly sensitive response to small changes in the detection target (e.g., hydrogen) in the atmosphere. For example, an ultra-sensitive hydrogen sensor can be obtained.

For example, the second layer 32 does not include the first element. Alternatively, the concentration of the first element in the second layer 32 is lower than the concentration of the first element in the first layer 31.

For example, the first layer 31 does not include the second element. Alternatively, the concentration of the second element in the first layer 31 is lower than the concentration of the second element in the second layer 32.

For example, the first element can be reduced by the detection target gas. The second element is not substantially reduced by the detection target gas. In one example, the detection target gas is hydrogen.

As shown in FIG. 1, the movable portion 30M may include a movable electrode 35 The capacitance may be the capacitance between the fixed electrode 55 and the movable electrode 35.

As shown in FIG. 2, the concentration of the detection target gas in the first state ST1 (high concentration) is higher than the concentration of the detection target gas in the second state ST2 (low concentration). The first capacitance between the fixed electrode 55 and the movable portion 30M in the first state ST1 is smaller than the second capacitance between the fixed electrode 55 and the movable portion 30M in the second state ST2.

Thus, the change in capacitance corresponds to the concentration of the detection target gas. The detection target gas can be detected by detecting the change in capacitance. For example, the target gas can be detected with a high sensitivity of about 0.1 ppm to 1000 ppm.

As shown in FIG. 1, the sensor 110 may further include a controller 70. The controller 70 is configured to detect the capacitance (for example, first capacitance, second capacitance, etc.).

The change in capacitance corresponds to the change in the distance dz between the fixed electrode 55 and the movable portion 30M (movable electrode 35). For example, a first distance between the fixed electrode 55 and the movable portion 30M in the first state ST1 (high concentration) is longer than a second distance between the fixed electrode 55 and the movable portion 30M in the second state ST2 (low concentration).

For example, the change in the distance dz may be detected. For example, the displacement of the movable portion 30M may be detected by an optical technique or the like.

As described above, the change in the distance dz may be based on the stress caused by the change in the volume of the first layer 31. For example, a first volume of the first layer 31 in the first state ST1 (high concentration) is smaller than a second volume of the first layer 31 in the second state ST2 (low concentration).

As shown in FIG. 1, in this example, the first support layer 31L is provided between the base 40 and the first layer 31. A second gap G2 is provided between the base 40 and the first support layer 31L.

In this example, the sensor 110 further includes a first connect portion 31c. A part of the first connect portion 31c is connected to the first support portion 31s. Another part of the first connect portion 31c is connected to the movable portion 30M. A third gap G3 is provided between the base 40 and the first connect portion 31c. For example, the first connect portion 31c may have a meandering structure.

As shown in FIG. 1, the sensor 110 may include a second fixed portion 22 and a second support portion 32s. The base 40 further includes a third region 43. The first region 41 is provided between the second region 42 and the third region 43. The second fixed portion 22 is fixed to the third region 43. The second support portion 32s is connected to the second fixed portion 22. The second support portion 32s includes a second support layer 32L, a third layer 33, and a fourth layer 34. The third layer 33 is fixed to the second support layer 32L. At least a part of the third layer 33 is provided between the second support layer 32L and the fourth layer 34.

The third layer 33 includes the first element and oxygen. The fourth layer 34 includes the second element and oxygen. The third layer 33 includes, for example, an oxide of the first element. The third layer 33 includes, for example, a bond of the first element and oxygen. The fourth layer 34 includes, for example, an oxide of the second element. The fourth layer 34 includes, for example, a bond of the second element and oxygen.

For example, the fourth layer 34 does not include the first element. Alternatively, the concentration of the first element in the fourth layer 34 is lower than the concentration of the first element in the third layer 33.

For example, the third layer 33 does not include the second element. Alternatively, the concentration of the second element in the third layer 33 is lower than the concentration of the second element in the fourth layer 34.

The movable portion 30M is provided between the first support portion 31s and the second support portion 32s. The movable portion 30M is supported by the first support portion 31s and the second support portion 32s. A fourth gap G4 is provided between the base 40 and the second support portion 32s. A double-sided beam type structure may be applied.

In this example, the sensor 110 further includes a second connect portion 32c. A part of the second connect portion 32c is connected to the second support portion 32s. Another part of the second connect portion 32c is connected to the movable portion 30M. A fifth gap G5 is provided between the base 40 and the second connect portion 32c. The second connect portion 32c has, for example, a meandering structure.

As shown in FIG. 1, the first support portion 31s may include a first conductive member 31h. The second support portion 32s may include a second conductive member 32h. For example, the temperature of the first support portion 31s can be increased by a current flowing through the first conductive member 31h. For example, the temperature of the second support portion 32s can be increased by a current flowing through the second conductive member 32h. For example, by heating the support portions, various substances (including, for example, hydrogen) adsorbed on the first support portion 31s and the second support portion 32s are released.

The thickness of the first layer 31 and the third layer 33 is, for example, not less than 1 nm and not more than 1 μm. The thickness of the second layer 32 and the fourth layer 34 is, for example, not less than 0.1 nm and not more than 1 μm. The thickness of the first support layer 31L and the second support layer 32L is, for example, not less than 10 nm and not more than 10 μm. The thicknesses corresponds to the length along the first direction D1.

The first support layer 31L and the second support layer 32L include, for example, silicon and at least one selected from the group consisting of nitrogen and oxygen. The first support layer 31L and the second support layer 32L may include silicon nitride or silicon oxide.

Figures 4, 5:
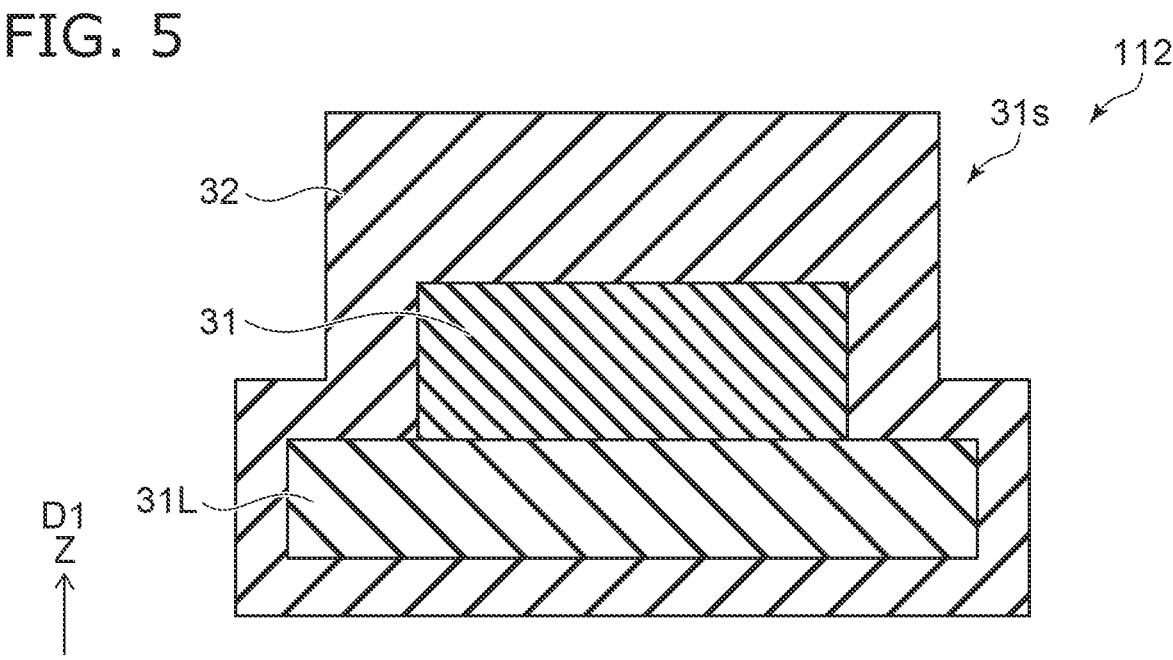
FIG. 4 is a schematic cross-sectional view illustrating a part of the sensor according to the first embodiment.
FIG. 5 is a schematic cross-sectional view illustrating a part of the sensor according to the first embodiment.

FIGS. 4 and 5 are schematic cross-sectional views illustrating a part of the sensor according to the first embodiment.

These figures illustrate the first support portion 31s. As shown in FIGS. 4 and 5, in a sensor 111 and a sensor 112 according to the embodiment, the configuration of the first support portion 31s is different from the configuration in the sensor 110. The configurations of the sensor 111 and the sensor 112 other than this may be the same as the configuration of the sensor 110.

As shown in FIG. 4, in the sensor 111, the first layer 31 is provided between a plurality of regions included in the second layer 32 in a direction crossing the first direction D1. For example, the upper face of the first layer 31 is covered with the second layer 32. The side faces of the first layer 31 may be covered with the second layer 32. In the first layer 31, the influence of oxygen is more effectively suppressed.

As shown in FIG. 5, in the sensor 112, at least a part of the first support layer 31L is provided between a part of the second layer and the first layer 31 in the first direction D1. For example, in the first direction D1, the first support layer 31L and the first layer 31 may be provided between a plurality of regions included in the second layer 32.

In the sensor 111 and the sensor 112, the configuration of the first support portion 31s may be applied to the second support portion 32s.

There are resistance change type or semiconductor type hydrogen sensors. In these hydrogen sensors, there is a limit to the reduction in power consumption.

In the embodiment, for example, the first layer 31 is reduced by the detection target gas (hydrogen). As a result, the first support portion 31s including the first layer 31 is deformed. The deformation of the first support portion 31s is detected as, for example, a change in capacitance.

In the embodiment, the first layer 31 (sensitive film) includes a metal oxide. Metal oxides have catalytic activity. When a reducing gas such as hydrogen approaches the sensitive film, the film stress changes in the direction of tensile stress. The concentration of oxygen in the sensitive film changes depending on the concentration (including the presence or absence) of the detection target gas.

For example, when the reducing gas such as hydrogen approaches the sensitive membrane, hydrogen molecules dissociate into hydrogen atoms on the surface of the sensitive film. This hydrogen atom reduces the metal oxide and leaves forming water. The frequency of this reaction depends on the hydrogen concentration. When the amount of oxygen in the sensitive film decreases, the film stress changes in the tensile direction.

In the embodiments, for example, the reducing action of catalytic metal oxides is utilized. For example, the metal oxide is reduced by the reducing gas of the detection target gas. Thereby, the volume of the layer including the catalytic metal changes. The change in volume is detected as a change in capacitance. By utilizing the reducing action, the concentration of a very small amount of reducing gas, about 0.1 ppm, can be detected with high sensitivity.

The embodiments may include the following technical proposals.

(Technical Proposal 1)

A sensor, comprising:

a base including a first region and a second region;

a fixed electrode fixed to the first region;

a first fixed portion fixed to the second region;

a first support portion connected to the first fixed portion, the first support portion including a first support layer, a first layer, and a second layer, the first layer being provided between the first support layer and at least a part of the second layer in a first direction from the first support layer to the second layer, the first layer including oxygen and a first element including at least one selected from the group consisting of Pt, Pd and Ti, the second layer including oxygen and a second element different from the first element; and a movable portion supported by the first support portion, a first gap being provided between the fixed electrode and the movable portion.

(Technical Proposal 2)

The sensor according to Technical Proposal 1, wherein the second element includes at least one selected from the group consisting of Si and Al.

(Technical Proposal 3)

The sensor according to Technical Proposal 1 or 2, wherein the second layer does not include the first element, or a concentration of the first element in the second layer is lower than a concentration of the first element in the first layer.

(Technical Proposal 4)

The sensor according to Technical Proposal 3, wherein the first layer does not include the second element, or a concentration of the second element in the first layer is lower than a concentration of the second element in the second layer.

(Technical Proposal 5)

The sensor according to any one of Technical proposals 1-4, wherein the first layer is provided between a plurality of regions included in the second layer in a direction crossing the first direction.

(Technical Proposal 6)

The sensor according to any one of Technical proposals 1-5, wherein at least a part of the first support layer is provided between a part of the second layer and the first layer in the first direction.

(Technical Proposal 7)

The sensor according to any one of Technical proposals 1-6, wherein the first layer is reduced by a detection target gas around the first support portion.

(Technical Proposal 8)

The sensor according to Technical Proposal 7, wherein the detection target gas includes hydrogen.

(Technical Proposal 9)

The sensor according to any one of Technical proposals 1-6, wherein a concentration of a detection target gas in a first state is higher than a concentration of the detection target gas in a second state, and a first distance between the fixed electrode and the movable portion in the first state is longer than a second distance between the fixed electrode and the movable portion in the second state.

(Technical Proposal 10)

The sensor according to any one of Technical proposals 1-6, wherein a concentration of a detection target gas in a first state is higher than a concentration of the detection target gas in a second state, and a first volume of the first layer in the first state is smaller than a second volume of the first layer in the second state.

(Technical Proposal 11)

The sensor according to any one of Technical proposals 1-6, wherein a concentration of a detection target gas in a first state is higher than a concentration of the detection target gas in a second state, and a first capacitance between the fixed electrode and the movable portion in the first state is smaller than a second capacitance between the fixed electrode and the movable portion in the second state.

(Technical Proposal 12)

The sensor according to Technical Proposal 11, further comprising:

a controller configured to detect the first capacitance and the second capacitance.

(Technical Proposal 13)

The sensor according to any one of Technical proposals 1-12, wherein the first layer includes a bond of the first element and oxygen, and the second layer includes a bond of the second element and oxygen.

(Technical Proposal 14)

The sensor according to any one of Technical proposals 1-13, wherein the first support portion further includes a first conductive member, and a temperature of the first support portion is configured to be increased by a current flowing through the first conductive member.

(Technical Proposal 15)

The sensor according to any one of Technical proposals 1-14, wherein the first support layer includes silicon and at least one selected from the group consisting of nitrogen and oxygen.

(Technical Proposal 16)

The sensor according to any one of Technical proposals 1-15, wherein the first support layer is provided between the base and the first layer, and a second gap is provided between the base and the first support layer.

(Technical Proposal 17)

The sensor according to Technical Proposal 16, further comprising:

a first connect portion, a part of the first connect portion being connected to the first support portion, another part of the first connect portion being connected to the movable portion, and a third gap being provided between the base and the first connect portion.

(Technical Proposal 18)

The sensor according to any one of Technical proposals 1-17, further comprising:

a second fixed portion; and a second support portion, the base further including a third region, the first region being provided between the second region and the third region, the second fixed portion being fixed to the third region, the second support portion being connected to the second fixed portion, the second support portion including a second support layer, a third layer fixed to the second support layer, and a fourth layer, at least a part of the third layer being provided between the second support layer and the fourth layer, the third layer including the first element and oxygen, the fourth layer including the second element and oxygen, and the movable portion being provided between the first support portion and the second support portion, and being further supported by the second support portion.

(Technical Proposal 19)

The sensor according to Technical Proposal 18, further comprising:

a second connect portion, a part of the second connect portion being connected to the second support portion, another part of the second connect portion being connected to the movable portion, and a gap being provided between the base and the second connect portion.

(Technical Proposal 20)

The sensor according to any one of Technical proposals 1-19, wherein a thickness of the first layer is not less than 1 nm and not more than 1 μm, a thickness of the second layer is not less than 0.1 nm and not more than 1 μm, and a thickness of the first support layer is not less than 10 nm and not more than 10 μm.

According to the embodiment, it is possible to provide a sensor that provides high detection sensitivity.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in the sensors such as bases, fixed portions, support portions, layers, movable portions, fixed electrodes, controllers, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors practicable by an appropriate design modification by one skilled in the art based on the sensors described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:

a base including a first region and a second region;

a fixed electrode fixed to the first region;

a first fixed portion fixed to the second region;

a first support portion connected to the first fixed portion, the first support portion including a first support layer, a first layer, and a second layer, the first layer being provided between the first support layer and at least a part of the second layer in a first direction from the first support layer to the second layer, the first layer including oxygen and a first element including at least one selected from the group consisting of Pt, Pd and Ti, the second layer including oxygen and a second element different from the first element; and a movable portion supported by the first support portion, a first gap being provided between the fixed electrode and the movable portion.

2. The sensor according to claim 1, wherein the second element includes at least one selected from the group consisting of Si and Al.

3. The sensor according to claim 1, wherein the second layer does not include the first element, or a concentration of the first element in the second layer is lower than a concentration of the first element in the first layer.

4. The sensor according to claim 3, wherein the first layer does not include the second element, or a concentration of the second element in the first layer is lower than a concentration of the second element in the second layer.

5. The sensor according to claim 1, wherein the first layer is provided between a plurality of regions included in the second layer in a direction crossing the first direction.

6. The sensor according to claim 1 wherein at least a part of the first support layer is provided between a part of the second layer and the first layer in the first direction.

7. The sensor according to claim 1, wherein the first layer is reduced by a detection target gas around the first support portion.

8. The sensor according to claim 7, wherein the detection target gas includes hydrogen.

9. The sensor according to claim 1, wherein a concentration of a detection target gas in a first state is higher than a concentration of the detection target gas in a second state, and a first distance between the fixed electrode and the movable portion in the first state is longer than a second distance between the fixed electrode and the movable portion in the second state.

10. The sensor according to claim 1, wherein a concentration of a detection target gas in a first state is higher than a concentration of the detection target gas in a second state, and a first volume of the first layer in the first state is smaller than a second volume of the first layer in the second state.

11. The sensor according to claim 1, wherein a concentration of a detection target gas in a first state is higher than a concentration of the detection target gas in a second state, and a first capacitance between the fixed electrode and the movable portion in the first state is smaller than a second capacitance between the fixed electrode and the movable portion in the second state.

12. The sensor according to claim 11, further comprising: a controller configured to detect the first capacitance and the second capacitance.

13. The sensor according to claim 1, wherein the first layer includes a bond of the first element and oxygen, and the second layer includes a bond of the second element and oxygen.

14. The sensor according to claim 1, wherein the first support portion further includes a first conductive member, and a temperature of the first support portion is configured to be increased by a current flowing through the first conductive member.

15. The sensor according to claim 1, wherein the first support layer includes silicon and at least one selected from the group consisting of nitrogen and oxygen.

16. The sensor according to claim 1, wherein the first support layer is provided between the base and the first layer, and a second gap is provided between the base and the first support layer.

17. The sensor according to claim 16, further comprising:

a first connect portion, a part of the first connect portion being connected to the first support portion, another part of the first connect portion being connected to the movable portion, and a third gap being provided between the base and the first connect portion.

18. The sensor according to claim 1, further comprising:

a second fixed portion; and a second support portion, the base further including a third region, the first region being provided between the second region and the third region, the second fixed portion being fixed to the third region, the second support portion being connected to the second fixed portion, the second support portion including a second support layer, a third layer fixed to the second support layer, and a fourth layer, at least a part of the third layer being provided between the second support layer and the fourth layer, the third layer including the first element and oxygen, the fourth layer including the second element and oxygen, and the movable portion being provided between the first support portion and the second support portion, and being further supported by the second support portion.

19. The sensor according to claim 18, further comprising:

a second connect portion, a part of the second connect portion being connected to the second support portion, another part of the second connect portion being connected to the movable portion, and a gap being provided between the base and the second connect portion.

20. The sensor according to claim 1, wherein a thickness of the first layer is not less than 1 nm and not more than 1 μm, a thickness of the second layer is not less than 0.1 nm and not more than 1 μm, and a thickness of the first support layer is not less than 10 nm and not more than 10 μm.

\* \* \* \* \*